United States Patent
de Rose et al.

(10) Patent No.: US 10,307,405 B2
(45) Date of Patent: Jun. 4, 2019

(54) STABLE VETERINARY COMBINATION FORMULATIONS OF MACROCYCLIC LACTONES AND IMIDAZOTHIAZOLES

(71) Applicant: Zoetis Services LLC, Florham Park, NJ (US)

(72) Inventors: Guy Francis de Rose, Kalamazoo, MI (US); Sachin Pundlik Kolhe, Mumbai (IN)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 14/779,045

(22) PCT Filed: Apr. 10, 2014

(86) PCT No.: PCT/US2014/033599
§ 371 (c)(1),
(2) Date: Sep. 22, 2015

(87) PCT Pub. No.: WO2014/169092
PCT Pub. Date: Oct. 16, 2014

(65) Prior Publication Data
US 2016/0051524 A1  Feb. 25, 2016

Related U.S. Application Data

(60) Provisional application No. 61/811,138, filed on Apr. 12, 2013.

(51) Int. Cl.
| | | |
|---|---|---|
| *A61K 31/7048* | (2006.01) | |
| *A61K 31/429* | (2006.01) | |
| *A61K 31/415* | (2006.01) | |
| *A61K 45/00* | (2006.01) | |
| *A61K 9/00* | (2006.01) | |
| *A61K 31/365* | (2006.01) | |
| *A61K 31/4184* | (2006.01) | |
| *A61K 47/26* | (2006.01) | |

(52) U.S. Cl.
CPC .......... *A61K 31/429* (2013.01); *A61K 9/0017* (2013.01); *A61K 9/0019* (2013.01); *A61K 31/365* (2013.01); *A61K 31/415* (2013.01); *A61K 31/4184* (2013.01); *A61K 31/7048* (2013.01); *A61K 45/00* (2013.01); *A61K 47/26* (2013.01)

(58) Field of Classification Search
CPC .............. A61K 31/429; A61K 31/7048; A61K 31/365; A61K 47/26; A61K 31/4184
USPC ..................................................... 514/30, 368
See application file for complete search history.

(56) References Cited

U.S. PATENT DOCUMENTS

| | | | |
|---|---|---|---|
| 4,144,352 A | 3/1979 | Putter | |
| 4,199,569 A | 4/1980 | Chabala et al. | |
| 4,310,519 A | 1/1982 | Albers-Schonberg et al. | |
| 4,791,134 A | 12/1988 | Burckhardt | |
| 4,916,154 A | 4/1990 | Asato et al. | |
| 6,653,342 B2 | 11/2003 | Saito et al. | |
| 7,348,417 B2 | 3/2008 | Sorokin et al. | |
| 2011/0245191 A1* | 10/2011 | Rosentel, Jr. .......... | A01N 43/60 514/30 |
| 2013/0143956 A1* | 6/2013 | Cady .................... | C07D 493/22 514/450 |

FOREIGN PATENT DOCUMENTS

| | | |
|---|---|---|
| WO | 2005/063015 A2 | 7/2005 |
| WO | 2006/006021 A2 | 1/2006 |
| WO | 2006/069580 A1 | 7/2006 |
| WO | 2009/070687 A1 | 6/2009 |
| WO | 2010/021555 A1 | 2/2010 |
| WO | 2011/143479 A1 | 11/2011 |

OTHER PUBLICATIONS

Glossary of medical education terms, Institute of International Medical Education. http://www.iime.org/glossary.htm Accessed in Mar. 2013.*

Sargison et al. Failure of moxidectin to control benzimidazole-, levamisole- and ivermectinresistant Teladorsagia circumcincta in a sheep flock. Veterinary Record (2005) 156, 105-109.*

* cited by examiner

*Primary Examiner* — Yih-Horng Shiao
(74) *Attorney, Agent, or Firm* — Paul M. Misiak

(57) ABSTRACT

The present invention is directed to stabilized compositions comprising at least one macrocyclic lactone, or derivative thereof, in combination with levamisole, and an amino sugar stabilizing agent, optionally an additional antiparasitic agent, and a method for treating or controlling a parasitic infection or infestation in an animal by administering said composition.

14 Claims, No Drawings

STABLE VETERINARY COMBINATION FORMULATIONS OF MACROCYCLIC LACTONES AND IMIDAZOTHIAZOLES

CROSS-REFERENCE TO RELATED APPLICATIONS

This application is a US National Stage entry of International Application No. PCT/US2014/033599, filed Apr. 10, 2014, which claims the benefit of U.S. Provisional Application No. 61/811,138, filed Apr. 12, 2013.

FIELD OF INVENTION

This invention relates to compositions with enhanced stability for combating ectoparasites and endoparasites in and on animals, comprising a macrocyclic lactone or derivative thereof, levamisole, an amino sugar stability enhancer, and a pharmaceutically or veterinarily acceptable carrier or excipient, or mixture thereof, and optionally at least one additional active antiparasitic agent. The invention also provides for an improved method for eradicating, controlling, and preventing parasitic infections and infestations in or on an animal comprising administering the compositions of the invention to the animal in need thereof.

BACKGROUND OF INVENTION

Animals such as mammals and birds are often susceptible to endoparasitic and/or ectoparasitic infection and infestation. Ectoparasites include fleas, ticks, mites, lice, mosquitoes and flies, all of which can adversely affect the health of the animal. Endoparasites, those parasites that live within the host animal also adversely affect the health of the infected animal. Helminthiasis, which is most frequently caused by a group of parasitic worms categorized as cestodes (tapeworm), nematodes (roundworm) and trematodes (flatworm or flukes) are all examples of endoparasites.

Anthelmintic and ectoparasitic agents have been effective against parasites, however, resistance to single antiparasitic compounds is becoming common. Combinations of these agents have been introduced as a means for gaining a broader range of parasitic control as well as in defense of the rising rates of resistance.

There are technical challenges for preparing a stable liquid composition comprising a macrocyclic lactone or derivative thereof, with at least one other antiparasitic agent, for example an imidathiazole. WO 2009/070687 discloses a pour-on composition with a macrocyclic lactone and clorsulon with a stability enhancer. The application recites that certain antiparasitic agents degrade without the presence of a stability enhancer, for example, glycerol formal and polyethylene glycol. WO2010/021555 recites a stabilized formulation comprising a macrocyclic lactone, levamisole, or an equivalent agent, and a modified starch as a stabilizer (i.e. hydroxypropyl starch phosphate). WO 2011/143479 discloses a formulation approach for an injectable solution comprising a system of solvents, including at least one surfactant, combined to produce a micellar solution that is relatively stable and suitable for injection. While these references disclose the use of various solvents, surfactants, and stability enhancers, none disclose the use of an amino sugar as a stability enhancer, particularly for use as an oral, topical, and injectable composition.

The combination of a macrocyclic lactone with levamisole, particularly acidic salts of levamisole, presents a number of challenges from a formulation solubility and stability perspective, as levamisole is known to be acid-stable, while the macrocyclic lactones are acid labile and are subject to hydrolytic degradation. Macrocyclic lactones, or derivatives thereof, such as doramectin, selamectin, milbemycin, and moxidectin, are stable at a neutral pH. The present invention describes the use of a stability enhancing amino sugar across a wide range of antiparasitic agent concentrations that can provide an efficacious veterinary dosage form with suitable solubility, stability, and shelf life, thereby allowing for increased antiparasitic efficacy and reduced resistance.

SUMMARY OF THE INVENTION

The present invention is directed to stabilized compositions comprising at least one macrocyclic lactone, or derivative thereof, in combination with levamisole, and an amino sugar stabilizing agent. In accordance with this invention, it has been discovered that these compositions generally show increased stability of the active agents, regardless of the active agent concentrations. Increased stability correlates with increased solubility and optimally, efficacy.

In another aspect of the invention, the composition comprises a veterinary composition comprising a therapeutically effective amount of a macrocyclic lactone, or derivative thereof, a therapeutically effective amount of levamisole, a stabilizing amino sugar, a pharmaceutically or veterinarily acceptable carrier or excipient, or mixture thereof, and optionally, at least one additional antiparasitic agent.

In yet another aspect of the invention, the composition comprises a veterinary composition comprising a therapeutically effective amount of a macrocyclic lactone, or derivative thereof, a therapeutically effective amount of levamisole, a stability enhancing amino sugar, a pharmaceutically or veterinarily acceptable carrier or excipient, or mixture thereof, and at least one additional antiparasitic agent.

In yet another aspect of the invention, the additional antiparasitic agent is a benzimidazole. The preferred benzimidazole is albendazole.

In yet another aspect, the invention is a method for treating a parasitic infection or infestation in an animal, by administering a composition of the present invention, to the animal in need thereof.

In yet another aspect of the invention, the composition is administered topically, orally, or by injection to the animal in need thereof.

The presence of an amino sugar in the composition surprisingly avoids the hydrolytic degradation of the macrocyclic lactone normally observed in the presence of acidic compounds such as levamisole hydrochloride, without significantly impacting the stability of the levamisole.

DEFINITIONS

For purposes of the present invention, as described and claimed herein, the following terms and phrases are defined as follows:

"Additional antiparasitic agent(s)" as used herein, unless otherwise indicated, refers to at least one other veterinary or pharmaceutical compound or product that provides a therapeutically effective amount of compound or product that are useful for the treatment of a parasitic infection or infestation in or on an animal, as described herein.

"Animal", as used herein, unless otherwise indicated, refers to an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, and horse. Preferred companion animals are dog and cat. More preferred is dog. Non-exclusive examples of livestock include: pig, llama, rabbits, goat, sheep, deer, elk, cattle, and bison. Preferred livestock is cattle and sheep.

"Infection" or Infestation", as used herein, unless otherwise indicated, refers to the state or condition of having parasites on or in the body.

"Macrocyclic lactone" or "derivative thereof" as used herein, designates a pharmaceutical or veterinary compound in the avermectin or milbemycin family of compounds including, avermectins, for example, ivermectin, abamectin doramectin, eprinomectin, selamectin, and the like; and milbemycins, for example milbemycin D, milbemycin oxime, moxidectin, and the like.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms of the Arthropoda phylum (e.g., arachnids and insects) which feed through or upon the skin of its host. Preferred arachnids are of the order Acarina, e.g., ticks and mites. Preferred insects are midges, fleas, mosquitoes, biting flies (stable fly, horn fly, blow fly, horse fly, and the like), bed bugs, and lice. Preferred compositions of the present invention can be used for the treatment of parasites, i.e., treatment of a parasitic infection or infestation. Parasite(s) also encompasses the different life stages of the ectoparasite and endoparasite, including eggs, pupae, and larvae which feed on or in the body.

"Stability Enhancer(ing)", as used herein, unless otherwise indicated, refers to an amount of an amino sugar, as defined herein, that imparts enhanced stability to the active antiparasitic agent(s) and to the composition.

"Therapeutically effective amount", as used herein, unless otherwise indicated, refers to an amount of one or combination of at least one additional antiparasitic agent of the present invention that (i) treat or prevent the particular parasitic infection or infestation, (ii) attenuates, ameliorates, or eliminates one or more symptoms of the particular parasitic infestation, or (iii) prevents or delays the onset of one or more symptoms of the particular parasitic infestation described herein.

"Treatment", "treating", and the like, as used herein, unless otherwise indicated, refers to reversing, alleviating, or inhibiting the parasitic infection, infestation, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to an animal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

"Veterinary acceptable" as used herein, unless otherwise indicated, indicates that the substance or composition must be compatible chemically and/or toxicologically, with the other ingredients comprising a formulation, composition, and/or the animal being treated therewith. The term "pharmaceutically" acceptable has the same meaning as that recited for "veterinarily" acceptable.

"% w/w" herein refers to the mass fraction of a given composition component expressed as a percentage, determined according to the formula $m_i/m_{tot} \times 100$, wherein $m_i$ is the mass of the substance of interest present in the composition, and $m_{tot}$ is the total mass of the composition.

DETAILED DESCRIPTION

The present invention provides novel and inventive antiparasitic compositions comprising a macrocyclic lactone, or derivative thereof, levamisole, together with a pharmaceutically or veterinarily acceptable carrier, a stability enhancer, and optionally, at least one additional antiparasitic agent. The compositions include topical formulations, injectable formulations, and oral formulations, all of which have different concentrations of the active antiparasitic agents. These compositions provide surprisingly effective stability profiles.

Also provided are methods and uses for the treatment and/or control of parasitic infections or infestations in animals, comprising administering an effective amount of a formulation of the invention to the animal in need thereof.

The invention includes at least the following features:

(1) stable topical veterinary formulations comprising a macrocyclic lactone, or derivative thereof, in combination with levamisole, a stability enhancer, together with a pharmaceutically or veterinarily acceptable carrier or excipient, or mixture thereof, and optionally at least one additional antiparasitic agent, that is suitable for topical administration to an animal;

(2) stable oral veterinary formulations comprising a macrocyclic lactone, or derivative thereof, in combination with levamisole, a stability enhancer, together with a pharmaceutically or veterinarily acceptable carrier or excipient, or mixture thereof, and optionally at least one additional antiparasitic agent, that is suitable for oral administration to an animal;

(3) stable injectable veterinary formulations comprising a macrocyclic lactone, or derivative thereof, in combination with levamisole, a stability enhancer, together with a pharmaceutically or veterinarily acceptable carrier or excipient, or mixture thereof, and optionally at least one additional antiparasitic agent, that is suitable for injectable administration to an animal;

(4) methods for the treatment or control of a parasitic infection or infestation in an animal comprising administering an effective amount of a composition comprising a macrocyclic lactone, or derivative thereof, in combination with levamisole, a stability enhancer, together with a pharmaceutically or veterinarily acceptable carrier or excipient, or mixture thereof, and optionally, at least one additional antiparasitic agent, that is suitable for topical application to an animal;

(5) methods for the treatment or control of a parasitic infection or infestation in an animal comprising administering an effective amount of a composition comprising a macrocyclic lactone, or derivative thereof, in combination with levamisole, a stability enhancer, together with a pharmaceutically or veterinarily acceptable carrier or excipient, or mixture thereof, and optionally, at least one additional antiparasitic agent, that is suitable for oral administration to an animal;

(6) methods for the treatment or control of a parasitic infection or infestation in an animal comprising administering an effective amount of a composition comprising a macrocyclic lactone, or derivative thereof, in combination with levamisole, a stability enhancer, together with a pharmaceutically or veterinarily acceptable carrier or excipient, or mixture thereof, and optionally, at least one additional antiparasitic agent, that is suitable for injectable administration to an animal;

(7) use of a veterinary composition comprising a macrocyclic lactone, or derivative thereof, in combination with levamisole, a stability enhancer, together with a pharmaceutically or veterinarily acceptable carrier or excipient, or mixture thereof, and optionally at least one additional antiparasitic agent, that is suitable for oral, topical, and injectable administration to an animal for the treatment and control of a parasitic infection or infestation;

(8) a method for treating a parasitic infection or infestation in an animal in need thereof, by administering an effective amount of a composition of the present invention; and (9) the enhanced stability of the oral, topical, and injectable compositions of the present invention by addition of a stability enhancing amino sugar.

It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents.

The present invention provides for a veterinary composition for the treatment of a parasitic infection or infestation in an animal which comprises administering a veterinarily effective amount of a composition comprising a macrocyclic lactone, or derivative thereof, in combination with levamisole, an amino sugar stability enhancer, and a pharmaceutically or veterinarily acceptable carrier or excipient, or mixture thereof, and optionally, at least one additional antiparasitic agent.

Veterinary compositions suitable for the delivery of the compositions of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The present invention recites numerous US patent numbers and WO publication numbers, all of which are hereby incorporated by reference in their entirety.

In the present invention, the macrocyclic lactone, or derivative thereof, includes avermectins and the milbemycins. Avermectins and milbemycins share the same common 16-membered macrocyclic lactone ring; however, milbemycins do not possess the disaccharide substituent on the 13-position of the lactone ring. In addition to treating parasitic insects, avermectins and milbemycins are used to treat endoparasites, e.g., round worm infections, in animals. The avermectin and milbemycin series of compounds are natural products and can be prepared by semi-synthetic procedures known to those skilled in the art. Some of the natural product avermectins are disclosed in U.S. Pat. No. 4,310,519, and the 22,23-dihydro avermectin compounds are disclosed in U.S. Pat. No. 4,199,569. Non-limiting examples of avermectins include: abamectin, dimadectin, doramectin, emamectin, eprinomectin, ivermectin, latidectin, lepimectin, and selamectin. The milbemycins are the aglycone derivatives of the avermectins, such as those described, for example in U.S. Pat. Nos. 4,144,352, 4,791, 134, and 6,653,342. Particularly important anthelmintics of this family include moxidectin, as described, for example in U.S. Pat. Nos. 7,348,417; and 4,916,154. Non-limiting examples of milbemycins include milbemectin, milbemycin D, milbemycin oxime, nemadectin, and moxidectin. Therapeutically effective amounts of a macrocyclic lactone, or derivative thereof, for purposes of this invention, range from about 0.1% w/w to about 1% w/w.

The macrocyclic lactones, and derivatives thereof, are antiparasitic compounds that can be used for treating endo- and ectoparasitic infections and infestations in animals. In addition, the macrocyclic lactones can be combined with the antiparasitic compound, levamisole. Levamisole belongs to a class of synthetic imidathiazole derivatives which are used as anthelmintics. Levamisole is highly effective against common gastrointestinal nematodes and lungworms and many larval stages of other worms in ruminants. In swine, levamisole is effective against both adult and immature stages of *Ascaris suum*. As used within the scope of the present invention, levamisole, or a pharmaceutically or veterinarily acceptable salt thereof, refers to inorganic salts of levamisole such as hydrochloride or phosphate salts, and does not include organic salts, such as disophenol or nitroxinil salts of levamisole. Amounts of levamisole or its salts as used herein, refer to % w/w expressed as salt equivalents, without regard to the contribution of the particular salt counterion to the total mass. Therapeutically effective amounts of levamisole for purposes of this invention range from about 4% w/w to about 24% w/w.

In addition to the macrocyclic lactone, or derivative thereof, in combination with levamisole, the compositions of the instant invention can further comprise an additional antiparasitic agent. The additional antiparasitic agent is contemplated as a benzimidazole. The benzimidazoles are bicyclic, heterocyclic aromatic organic compounds, consisting of the fusion of benzene and imidazole. Examples of benzimidazole derivatives useful in the practice of the present invention include, but are not limited to, albendazole, mebendazole, cambendazole, fenbendazole, flubendazole, mebendazole, oxfendazole, oxibendazole, parbendazole, thiabendazole, triclabendazole, and the like. The preferred benzimidazole is albendazole. A therapeutically effective amount of a benzimidazole for purposes of this invention ranges from about 1% w/w to about 5% w/w. The preferred amount is about 2.4% w/w.

As described herein, the combination of an acid labile macrocyclic lactone, or derivative thereof, with the imidathiazole, levamisole, is best protected with the use of a stability enhancer. Stability enhancers including glycerol formal, glycol ethers, and modified starches, for example hydroxypropyl starch phosphate, have been described previously. Triethanolamine can also be used as a stability enhancer. The present invention describes the use of an amino sugar as a stability enhancer. Examples of amino sugars useful in the practice of the present invention include, but are not limited to glucosamine, tromethamine, and meglumine. The preferred amino sugar is meglumine. Meglumine is an amino sugar derived from sorbitol. Further, meglumine is an organic base used as a pH adjusting agent and solubilizing agent in liquid pharmaceutical preparations.

In some embodiments, the solvent systems of the invention advantageously broaden the efficacy of a pharmaceutical or veterinary composition by providing enhanced solvency for one or more of the active agents. For example, by providing a solvent system that enhances the solvency of an active agent, such as a parasiticidal agent, an increased amount of the active agent can be incorporated into the composition for administration to an animal.

In certain embodiments, this invention provides pharmaceutically and veterinarily acceptable compositions for the treatment of a parasitic infection or infestation in animals, comprising, a macrocyclic lactone, or derivative thereof, levamisole, an amino sugar stability enhancer, and one or more pharmaceutically or veterinarily acceptable carriers or excipients, or mixtures thereof, and optionally, at least one additional antiparasitic agent.

In certain embodiments, the formulations of the invention comprise a stability enhancing amount of an amino sugar selected from the group consisting of glucosamine, tromethamine, and meglumine.

In another embodiment, the formulations of the invention comprise a stability enhancing amount of meglumine. A stability enhancing amount of meglumine ranges from about 0.01% w/w to about 0.2% w/w. The preferred range is about 0.025% w/w to about 0.15% w/w.

In some embodiments, the stability of a composition of the invention is enhanced, in that no more than 6.0% degradation of the macrocyclic lactone is demonstrated when the composition is stored at 40° C. for 12 weeks, as compared to 56% degradation of the unstabilized composition stored under the same conditions.

In certain embodiments, one or more pharmaceutically or veterinarily acceptable carriers are employed to enhance the solubility of the active agent(s) in the composition. Similarly, these carriers are also chosen in view of the final route of administration contemplated for the composition. The compositions can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X). The compositions of the present invention are typically formulated into pharmaceutical and veterinary dosage forms to provide an easily controllable dosage form for administration. The choice of carrier, excipient, or mixture thereof, will to a large extent depend on factors such as the particular mode of administration, the effect of the carrier, excipient, or mixture thereof, on solubility and stability.

The compositions of the present invention are contemplated as liquid forms. Liquid forms include suspensions, solutions, syrups, drenches and elixirs. Liquid formulations may also be prepared by the reconstitution of a solid, for example, from a sachet or lyophilized sample. Oral drenches are commonly prepared by dissolving or suspending the active ingredient in a suitable medium.

Topical formulations include pour-on, spot-on, multi-spot-on, stripe-on, comb-on, roll-on, dip, spray, mousse, shampoo, powder formulation, gels, hydrogels, lotions, solutions, creams, ointments, foams, films, and micro emulsions. The injectable and oral compositions are contemplated as a composition that is administered subcutaneously and by drench, respectively.

Non-exclusive examples of pharmaceutically or veterinarily acceptable carriers include: water, alcohol, mineral oil, glycerin, glycerol formal, miglyol, Kolliphor HS15 (polyglycol mono- and di-esters of 12-hydroxystearic acid), glycerol, ethylene glycol, propylene glycol, methoxypropanol, diethylene glycol monoethyl ether, diethylene glycol monomethyl ether, diethylene glycol monobutyl ether, tetraglycol, triethylene glycol, butyl diglycol, dimethylacetamide, dimethylformamide, n-methylformamide, dipropylene glycol n-butyl ether, ethanol, isopropanol, methanol, ethylene glycol monoethyl ether, ethylene glycol monomethyl ether, dipropyleneglycol monomethyl ether, dipropyleneglycol monomethyl ether, dipropyleneglycol monomethyl ether, triethylene glycol monoethyl ether, triethylene glycol monomethyl ether, polyethylene glycols, methoxypolyethylene glycols, polypropylene glycols, polybutylene glycols, diethylene monoethylether acetate, diethylene monobutylether acetate, monomethylacetamide, liquid polyoxyethylene glycols, 2-pyrrolidone, propylene carbonate, butylene carbonate, tetrahydrofurfuryl alcohol, solketal, xylene, dimethyl isosorbide, short-, medium- and long-chain, and aromatic fatty acids, for example, butyric acid, capric acid, succinic, adipic, sebacic, caprylic acid, lauric acid, myristic acid, strearic acid, linoleic acid, and benzoic acid, triglycerides, for example, castor oil, cottonseed oil, sesame oil, linseed oil, safflower oil, peanut oil, soybean oil, coconut oil, olive oil, corn oil, and almond oil. The pharmaceutically or veterinarily acceptable carriers can also include: glyceryl stearates, glyceryl hexanoates, caprylic/capric glycerides, triacetin, glyceryl cocoate, caprylic glycerides, glyceryl, glyceryl stearates, glyceryl hexanoates, glyceryl monooleate, glyceryl ricinoleate, capric glycerides, succinic acid, isopropyl myristate, ethyl oleate, ethyl laurate, dibutyl adipate, propylene glycol monocaprylate, propylene glycol monolaurate, spider esters, dibutyl sebacate, dibutyl adipate, 2-pyrrolidone, N-methyl pyrrolidone, azone, gamma-hexalactone, short-, medium-, and long-chain and aromatic alcohols, such as ethanol, isopropyl alcohol, butanol, hexanol, octanol, decanol, dodecanol, stearic, alcohol, oleic alcohol, and benzyl alcohol, non-ionic surfactants such as labrasol, HS15/kolliphor HS15, cremophor EL, Tweens, sodium lauryl sulfate, and sodium dodecyl sulfate, limonene, eucalyptol, and menthol.

In certain embodiments, the composition further comprises at least one pharmaceutically or veterinarily acceptable excipient. Non-limiting examples of pharmaceutically or veterinarily acceptable excipients include antioxidants, antimicrobial preservatives, pH adjusters, taste masking or flavorant compounds and/or preparations, dyes, binders, fillers, spreading agents, surfactants, precipitation inhibitors, and scavengers of water and peroxides.

Non-exclusive examples of antioxidants include: ascorbic acid, vitamin E (tocopherol), vitamin E derivatives, butylated hydroxanisole (BHA), and butylated hydroxytoluene (BHT), citric acid, propyl gallate, thioglycerol, and the like. Preferred antioxidants include BHA and BHT.

Non-exclusive examples of antimicrobial preservatives include: potassium sorbate, sodium benzoate, benzyl alcohol, parabens, benzoic acid, sorbic acid, propionic acid, benzalkonium chloride, thimerosal, and 4-chlorocresol.

Non-exclusive examples of pH adjusters include: citric acid, lactic acid, monoethanolamine, diethanolamine, and triethanolamine.

Non-exclusive examples of binders include: sucrose, lactose, starches, cellulose, modified cellulose such as microcrystalline cellulose, methylcellulose, cellulose ethers such as hydroxypropyl cellulose, sugar alcohols such as xylitol, sorbitol and maltitol, gelatin, and synthetic polymers such as polyvinylpyrrolidone, and polyethylene glycol.

Non-exclusive examples of fillers include: starch, pregelatized starch, cellulose, powdered cellulose, microcrystalline cellulose, dibasic calcium phosphate, calcium carbonate, lactose, sucrose, glucose, sugar alcohols such as mannitol and sorbitol, colloidal silicon dioxide, and magnesium stearate.

Non-exclusive examples of spreading agents include: siloxanes such as dimethyl polysiloxane, and indopols, such as polyisobutylene.

Non-exclusive examples of surfactants include: labrasol, Solutol HS15 (Kolliphor HS15), the cremaphors, spans and tweens.

Non-exclusive examples of precipitation inhibitors include: poloxamers, such as Pluronic F68 or Pluronic F127, polyvinylpyrrolidones, such as PVP K20 and K90, alginates, xanthans, and celluloses, such as methylcellulose and ethylcellulose.

The invention further provides for titration of the amount of stability enhancer that is added to the compositions of the invention. For example, in embodiments where the stability enhancer is meglumine, the amount of meglumine can be titrated, such that an optimal stability of an active agent (i.e., doramectin, moxidectin, levamisole, and albendazole) is achieved in the composition.

In another aspect, the invention provides a composition for the treatment of a parasitic infection or infestation in animals, which comprises: (a) an effective amount of at least one macrocyclic lactone, or derivative thereof; (b) an effective amount of levamisole or a pharmaceutically or veterinarily acceptable salt thereof; (c) an amino sugar stability enhancer; (d) at least one pharmaceutically or veterinarily acceptable carrier or excipient, or mixture thereof, and optionally, (e) at least one additional pharmaceutically or veterinarily acceptable excipient.

In yet another aspect, the invention provides a composition for the treatment of a parasitic infection or infestation in animals, which comprises: (a) an effective amount of at least one macrocyclic lactone, or derivative thereof; (b) an effective amount of levamisole, or a pharmaceutically or veterinarily acceptable salt thereof; (c) an effective amount of albendazole; (d) an amino sugar stability enhancer; and (e) at least one pharmaceutically or veterinarily acceptable carrier or excipient, or mixture thereof.

In yet another aspect, the invention provides a composition for the treatment of a parasitic infection or infestation in animals, which comprises: (a) an effective amount of at least one macrocyclic lactone, or derivative thereof; (b) an effective amount of levamisole, or a pharmaceutically or veterinarily acceptable salt thereof; (c) the amino sugar meglumine as a stabilizing agent; and (d) at least one pharmaceutically or veterinarily acceptable carrier or excipient, or mixture thereof.

In yet another aspect, the invention provides a composition for the treatment of a parasitic infection or infestation in animals, which comprises: (a) an effective amount of at least one macrocyclic lactone, or derivative thereof; (b) an effective amount of levamisole, or a pharmaceutically or veterinarily acceptable salt thereof; (c) an effective amount of albendazole; (d) the amino sugar meglumine as a stabilizing agent; and (e) at least one pharmaceutically or veterinarily acceptable carrier or excipient, or mixture thereof.

The compositions of the instant invention are useful as parasiticides for the control and treatment of parasitic infections and infestations in an animal. The veterinary compositions of the present invention have utility as an ectoparasiticide, in particular, as an acaricide and insecticide. They may, in particular, be used in the fields of veterinary medicine, livestock husbandry and the maintenance of public health: against acarines and insects which are parasitic upon animals. Some non-limiting examples of acarine and insect parasites include: ticks (e.g., *Ixodes* spp., *Rhipicephalus* spp., *Boophilus* spp., *Amblyomma* spp., *Hyalomma* spp., *Haemaphysalis* spp., *Dermacentor* spp., *Ornithodorus* spp., and the like); mites (e.g., *Dermanyssus* spp., *Sarcoptes* spp., *Psoroptes* spp., *Eutrombicula* spp., *Chorioptes* spp., *Demodex* spp., and the like); chewing and sucking lice (e.g., *Damalinia* spp., *Linognathus* spp., and the like); fleas (e.g., *Siphonaptera* spp., *Ctenocephalides* spp., and the like); and flies, mosquitoes, and midges (e.g., Order Diptera; *Aedes* spp., *Anopheles* spp., *Tabanidae* spp., *Haematobia* spp., *Stomoxys* spp., *Dermatobia* spp., *Simuliidae* spp., *Ceratopogonidae* spp., *Psychodidae* spp., *Cochliomyia* spp., *Muscidae* spp., *Hypoderma* spp., *Gastrophilus* spp., *Simulium* spp., and the like); true bugs (e.g., Order Hemiptera); cockroaches (*Periplaneta* spp, *Blatella* spp) and wasps and ants (*Hymenoptera* spp).

The veterinary compositions of the present invention are of particular value in the control of ectoparasites and insects which are injurious to, or spread or act as vectors of diseases in animals, for example those described herein, and more especially in the control of ticks, mites, lice, fleas, midges and biting, nuisance flies, that may cause, for example, leishmaniasis, demidicosis, Lyme, and borreliosis. They are particularly useful in controlling acarines and insects which feed on the skin or tissue or suck the blood of the animal, for which purpose they may be administered topically.

The compositions of the instant invention are also useful as endoparasiticides for the control and treatment of parasitic infections and infestations in an animal. They too may, in particular, be used in the fields of veterinary medicine, livestock husbandry and the maintenance of public health: against nematodes, cestodes, and trematodes which are parasitic upon animals. Helminthiasis is most frequently caused by a group of parasitic worms described as nematodes or roundworms. Other endoparasites which occur in the gastrointestinal tract of animals include *Ancylostoma, Anecator, Ascaris, Strongyloides, Trichinella, Capillaria, Roxocara, Toxascaris, Trichiris, Enterobius*, and parasites which are found in the blood or other tissues and organs such as filarial worms and the extraintestinal stages of *Strongyloides, Toxocara*, and *Trichinella*.

EXAMPLES

The advantages of the instant invention should be evident from the non-limiting exemplary illustrations of the stabilized and non-stabilized combination compositions comprising a macrocyclic lactone, or derivative thereof, and levamisole hydrochloride. Compositions described as "#a", for example 1a and 2a, are compositions without the stability enhancer meglumine. Compositions described as "#b", for example 1b and 2b, are compositions with the stability enhancer meglumine.

For each of the examples, the ingredients in the proportions shown were mixed together in an appropriate mixing vessel using techniques generally known in the art. The resulting solutions were filled into sealed glass vials, stored at 40° C. for up to 12 weeks and then tested by an appropriate High Performance Liquid Chromatography (HPLC) method to determine remaining potency of the macrocyclic lactone and levamisole components.

Table 1 illustrates Composition 1a and 1b, comprising doramectin, levamisole, the carriers benzyl alcohol and triethylene glycol, and the anti-oxidant BHT, with and without meglumine. After 12 weeks at 40° C. and ambient humidity, 44% of the label doramectin concentration remained in the formulation containing no meglumine, while 94% remained in the meglumine formulation.

Table 2 illustrates Composition 2a and 2b, comprising doramectin, levamisole, the carrier glycerol formal, and the anti-oxidant BHT, with and without meglumine. After 12 weeks at 40° C. and ambient humidity, only 90% of the label doramectin concentration remained in the formulation containing no meglumine, while 97% remained in the meglumine formulation.

Table 3 illustrates Composition 3a and 3b, comprising moxidectin, levamisole, the carriers benzyl alcohol, glycerol formal, and triethylene glycol, and the anti-oxidant BHT, with and without meglumine. After 12 weeks at 40° C. and ambient humidity, 84% of the label moxidectin concentration remained in the formulation containing no meglumine, while 92% remained in the meglumine formulation.

Table 4 illustrates Composition 4a and 4b, comprising doramectin, levamisole, the carriers benzyl alcohol, glycerol formal, and Cremophor EL, and the anti-oxidants BHA and BHT, with and without meglumine. After 4 weeks and 12 weeks, respectively, at 40° C. and 75% relative humidity, only 79% of the label doramectin concentration remained in the formulation containing no meglumine, while nearly 96% remained in the meglumine formulation.

As can be seen from the stability data in Tables 1, 2, 3, and 4 below, compositions containing meglumine exhibited significantly enhanced stability after up to 12 weeks at 40° C. as compared to compositions without meglumine. It is thus possible by way of the formulations of the present invention to provide stabilized pharmaceutical compositions comprising macrocyclic lactones, which avoid the instability known to be associated with macrocyclic lactone combination compositions. Importantly, the stable pharmaceutical or veterinary composition comprising a macrocyclic lactone, levamisole, one or more pharmaceutically and veterinarily acceptable carriers or excipients or mixtures thereof, and an amino sugar, such as meglumine, provides improved stability and shelf-life over the compositions for such veterinary combination formulations.

TABLE 1

Composition 1

| Formulation Component | Formulation 1a (% w/w) | Formulation 1b (% w/w) |
| --- | --- | --- |
| Doramectin | 0.1 | 0.1 |
| Levamisole hydrochloride | 4.0 | 4.0 |
| BHT | 0.25 | 0.25 |
| Meglumine | 0.0 | 0.05 |
| Benzyl Alcohol | 11.47 | 11.47 |
| Triethylene Glycol | 84.18 | 84.13 |
| % Doramectin remaining after 12 weeks at 40° C. | 44.0 | 94.0 |

TABLE 2

Composition 2

| Formulation Component | Formulation 2a (% w/w) | Formulation 2b (% w/w) |
| --- | --- | --- |
| Doramectin | 0.1 | 0.1 |
| Levamisole hydrochloride | 4.0 | 4.0 |
| BHT | 0.25 | 0.25 |
| Meglumine | 0.0 | 0.05 |
| Glycerol formal | 95.65 | 95.6 |
| % Doramectin remaining after 12 weeks at 40° C. | 90.0 | 97.0 |

TABLE 3

Composition 3

| Formulation Component | Formulation 3a (% w/w) | Formulation 3b (% w/w) |
| --- | --- | --- |
| Moxidectin | 0.5 | 0.5 |
| Levamisole HCl | 11.78 | 11.78 |
| BHT | 0.25 | 0.25 |
| Meglumine | 0.0 | 0.025 |
| Benzyl alcohol | 11.47 | 11.47 |
| Glycerol formal | 37.5 | 37.5 |
| Triethylene glycol | 38.5 | 38.47 |
| % Moxidectin remaining after 12 weeks at 40° C. | 84.0 | 92.0 |

TABLE 4

Composition 4

| Formulation Component | Formulation 4a (% w/w) | Formulation 4b (% w/w) |
| --- | --- | --- |
| Doramectin | 0.5 | 0.5 |
| Levamisole HCl | 9.4 | 9.4 |
| Meglumine | 0.0 | 0.15 |
| Cremophor EL | 3.0 | 0.0 |
| BHA | 0.01% | 0.01% |
| BHT | 0.01% | 0.01% |
| Benzyl alcohol | 2.0 | 2.0% |
| Glycerol formal | qs | qs |
| % Doramectin remaining after 12 weeks at 40° C. | 79.2* | 95.5 |

*This result is based on 4 weeks at 40° C.

The invention claimed is:

1. A stable injectable veterinary antiparasitic composition comprising:
    (a) a therapeutically effective amount of doramectin, wherein the doramectin is present in the composition in the amount of about 0.1% w/w to about 1% w/w;
    (b) a therapeutically effective amount of levamisole, or a pharmaceutically or veterinarily acceptable salt thereof, wherein the levamisole is present in the composition in the amount of about 4% w/w to about 24% w/w;
    (c) an amino sugar stability enhancer consisting of meglumine; and
    (d) at least one pharmaceutically or veterinarily acceptable carrier selected from the group consisting of benzyl alcohol, glycerol formal, triethylene glycol, and mixture thereof, and further comprising butylated hydroxyanisole, butylated hydroxytoluene, or mixture thereof.

2. The composition of claim 1, wherein the meglumine is present in the composition in the amount of about 0.01% w/w to about 0.2% w/w.

3. The composition of claim 1, wherein the levamisole is levamisole hydrochloride.

4. The composition of claim 1 wherein the at least one pharmaceutically or veterinarily acceptable carrier is selected from benzyl alcohol, triethylene glycol, or mixture thereof.

5. The composition of claim 1 wherein the at least one pharmaceutically or veterinarily acceptable carrier is glycerol formal.

6. A stable injectable veterinary antiparasitic composition comprising:

(a) a therapeutically effective amount of doramectin present in the composition in the amount of about 0.1% w/w to about 1% w/w;

(b) a therapeutically effective amount of levamisole, or a pharmaceutically acceptable salt thereof, present in the composition in the amount of about 4.0% w/w to about 24% w/w;

(c) an amino sugar stability enhancer consisting of meglumine, present in the composition in the amount of about 0.01% w/w to about 0.2% w/w; and (d) at least one pharmaceutically or veterinarily acceptable carrier selected from the group consisting of benzyl alcohol, glycerol formal, triethylene glycol, and mixture thereof, and further comprising butylated hydroxyanisole, butylated hydroxytoluene, or mixture thereof.

7. The composition of claim 6 wherein the at least one pharmaceutically acceptable carrier is selected from benzyl alcohol, triethylene glycol, or mixture thereof.

8. The composition of claim 6 wherein the at least one pharmaceutically or veterinarily acceptable carrier is glycerol formal.

9. A method for alleviating a parasitic infection in an animal, comprising administering to said animal in need thereof, a stable injectable composition comprising:

(a) a therapeutically effective amount of doramectin present in the composition in the amount of about 0.1% w/w to about 1% w/w;

(b) a therapeutically effective amount of levamisole, or a pharmaceutically acceptable salt thereof, present in the composition in the amount of about 4.0% w/w to about 24% w/w;

(c) an amino sugar stability enhancer consisting of meglumine; and (d) at least one pharmaceutically or veterinarily acceptable carrier selected from the group consisting of benzyl alcohol, triethylene glycol, glycerol formal, and mixture thereof, and further comprising butylated hydroxyanisole, butylated hydroxytoluene, or mixture thereof.

10. The method of claim 9 wherein the meglumine is present in the composition in the amount of about 0.01% w/w to about 0.2% w/w.

11. The method of claim 10 wherein the at least one pharmaceutically or veterinarily acceptable carrier is selected from benzyl alcohol, triethylene glycol, or mixture thereof.

12. The method of claim 10 wherein the at least one pharmaceutically or veterinarily acceptable carrier is glycerol formal.

13. The method of claim 9 wherein the animal is cattle or sheep.

14. The method of claim 9 wherein the composition is administered to the animal by subcutaneous injection.

* * * * *